United States Patent
Choudary et al.

(10) Patent No.: US 6,376,726 B1
(45) Date of Patent: Apr. 23, 2002

(54) PROCESS FOR THE PRODUCTION OF NITROAROMATIC COMPOUNDS FROM AROMATIC HYDROCARBONS USING MODIFIED CLAY CATALYSTS

(75) Inventors: Boyapati Manoranjan Choudary; Mannepalli Lakshmi Kantam; Mutyala Sateesh; Kottapalli Koteswara Rao; Kondapuram Vijaya Raghavan, all of Andhra Pradesh (IN)

(73) Assignee: Council of Scientific & Industrial Research, New Delhi (ID)

( * ) Notice: Subject to any disclaimer, the term of this patent is extended or adjusted under 35 U.S.C. 154(b) by 0 days.

(21) Appl. No.: 09/047,724

(22) Filed: Mar. 25, 1998

(30) Foreign Application Priority Data

Oct. 14, 1997 (IN) .......................... 2939/Del/97

(51) Int. Cl.[7] .............................................. C07C 205/00
(52) U.S. Cl. ....................................... 568/927; 568/936
(58) Field of Search .................................. 568/927, 936

(56) References Cited

U.S. PATENT DOCUMENTS 5,004,846 A * 4/1991 Sato et al. ................ 568/940
6,034,287 A * 4/2000 Choudary et al. .......... 568/927

FOREIGN PATENT DOCUMENTS

JP            63225339       *   9/1988

OTHER PUBLICATIONS

Choudary et al, Jounal of Molecular Catalysis (1994), 87 (1), 33–38.*
Chemical Abstracts, vol. 124, No. 55543p (1994).
Chemical Abstracts, vol. 85, No. 177048c (1975).
Chemical Abstracts, vol. 96, No. 180947c (1980).
Chemical Abstracts, vol. 94, No. 83754p (1981).
Chemical Abstracts, vol. 119, No. 270778w (1991).

* cited by examiner

*Primary Examiner*—Johann Richter
*Assistant Examiner*—J. Parsa
(74) *Attorney, Agent, or Firm*—Ladas & Parry

(57) ABSTRACT

The present invention relates to a process for the production of nitro line aromatic compounds from aromatic hydrocarbons using modified clay catalysts. This invention particularly relates to a process for nitration of aromatic hydrocarbons using modified clay catalysts without using $H_2SO_4$. The process for the preparation of nitro compounds from aromatic hydrocarbons using modified clay catalysts comprises nitrating aromatic hydrocarbons using fuming nitric acid in the molar ratio of nitric acid to aromatic hydrocarbon 0.3:1 to 1.2:1 in the presence of metal exchanged clay catalyst at 25° C. to 155° C. for 0.25 to 2.0 hours and recovering the corresponding nitro compounds.

4 Claims, No Drawings

PROCESS FOR THE PRODUCTION OF NITROAROMATIC COMPOUNDS FROM AROMATIC HYDROCARBONS USING MODIFIED CLAY CATALYSTS

This invention relates to a process for the production of nitroaromatic compounds from aromatic hydrocarbons using modified clay catalysts. This invention particularly relates to a process for nitration of aromatic hydrocarbons using modified clay catalysts without the use of $H_2SO_4$. Thus, this process totally eliminates disposal of salts formed consequent to the neutralization of sulphuric acid.

BACKGROUND OF THE INVENTION

Nitration has been an active area of industrial chemistry for over a century. Nitration process is used for the production of many large-volume chemicals such as nitrobenzene, nitrotoluenes and nitrochlorobenzenes, and other nitroaromatics. These nitroaromatics are vital intermediates for dyes, pharmaceuticals, perfumes and pesticides.

Nitration of aromatic hydrocarbons is performed classically with a mixture of nitric and sulfuric acids. One of the major disadvantages of this method is formation of by-products of polynitration and also causing environmental pollution during disposal of spent acid.

In the past, several methods were proposed for the nitration of aromatic hydrocarbons. For example, a U.S. Patent (U.S. Pat. No. 3,981,935; Sep. 21, 1976) discloses a two stage continuous process for benzene mononitration with $HNO_3$ and $H_2SO_4$. Another Japanese Patent (Jpn. Kokai Tokkyo Koho JP 8224,331; Feb. 8, 1982) gives a method in which chlorobenzene is nitrated with a mixture of $HNO_3$ and $H_2SO_4$ at 85–150° C. (p:o 61.45:37.8). A European Patent (EP 675,104; Oct. 4, 1995) describes a method for nitration of chlorobenzene at 60–160° C. using $HNO_3$ and $H_2SO_4$. Another Japanese Patent (Jpn. Kokai Tokkyo Koho JP 05,170,706; Jul. 9, 1993) describes a method for nitration of toluene with $HNO_3$ and $H_2SO_4$ at 0–50° C. (o:m:p 55:2.3:38.9). However, all these methods have a common disadvantage such as use of hazardous $H_2SO_4$, whose disposal poses a significant environmental problem. Although it has been known for some time that benzene and its homologs can be nitrated with $HNO_3$ alone, little or no progress has been made in this direction. The disadvantage in this method is the use of large excess of nitric acid (molar ratio of nitric acid to benzene are 2:1 to 4:1) which increases the possibility of poly-nitro compounds formation and affect the economics of the project.

Several catalytic methods are also known for nitration of aromatic hydrocarbons. Although these methods are practiced in laboratories, none of these methods have feasibility on a commercial basis in terms of economics and other factors. For example, a U.S. Patent (U.S. Pat. No. 4,234,470; Nov. 18, 1980) described a method for nitration of benzene, chlorobenzene and toluene with HNO3 in presence of Nafion catalyst. This method employs expensive Nafion resin whose activity is decreasing on each cycle.

Recently attention has been focused on the development of environmentally friendly solid acid catalysts such as zeolites, sulfated zirconia and Nafion especially in Friedel-Crafts reactions to replace environmentally hazardous chemicals, anhydrous aluminium chloride and sulfuric acid respectively in alkylation and nitration reactions.

SUMMARY OF THE INVENTION

The main objective of the present invention is the use of cheaply available modified montmorillonite, a smectite clay as a solid acid catalyst in the nitration of aromatic hydrocarbons. Cation exchange of interstitial cations with transition metal ions boosts the Lewis acidity.

Metal-exchanged montmorillonite catalysts were prepared as described in example 1 and employed in the nitration reactions on aromatic compounds, as described in examples 2–21.

DETAILED DESCRIPTION OF THE INVENTION

Accordingly the present invention provides:
1. A process for the preparation of nitroaromatic compounds from aromatic hydrocarbons using modified clay catalysts which comprises: nitrating aromatic hydrocarbons using fuming nitric acid in the molar ratio of nitric acid to aromatic hydrocarbon 0.3:1 to 1.2:1 in the presence of metal exchanged clay at 25°–155° C. for 0.25 to 2.0 hrs and recovering corresponding nitroaromatic compounds by conventional methods such as herein described.
2. The clay catalyst used is metal ion exchanged clay.
3. Various metal ions used are selected from $Al^{3+}$, $La^{3+}$, $Cu^{2+}$, $Fe^{3+}$ and $Zn^{2+}$.
4. Fuming nitric acid is used as the nitrating agent.
5. Aromatic hydrocarbons used are selected from benzene, chlorobenzene, toluene, o-xylene, m-xylene, p-xylene, anisole and naphthalene.
6. Recovery of nitroarenes is carried out by separating the catalyst by filtration and removing the excess aromatic hydrocarbons by distillation or by rotavapor.
7. A process for the preparation of nitroaromatic compounds from aromatic hydrocarbons using modified clay catalysts substantially as herein described with reference to examples 2 to 21.

The process of the present invention is illustrated with the following examples. However it should not limit the scope of the invention.

EXAMPLE 1

A series of catalysts were prepared.
a) K10 montmorillonite—Montmorillonite employed in the synthesis was obtained from Fluka (Grade K10) with exchange capacity of 0.8 equi.
b) Kunipia clay—Japanese clay (e.c., 1.15 equi.) was taken as it is without any modification.
c) i) $Fe^{3+}$—exchanged montmorillonite catalyst: To a 1 lt. stirred aqueous solution of $FeCl_3$ (1.0 M), 80 g of K10 montmorillonite was added. Stirring was maintained for 16–30 hrs in order to saturate the exchange capacity of montmorillonite K10. The clay suspension was centrifuged and the supernatant solution was discharged. The clay catalyst was filtered, and washed with distilled water and the washing cycles were repeated until disappearance of Cl ions from the discarded water. The clay was dried overnight in an oven at 120° C. and finely ground in a mortar.
ii) $Fe^{3+}$—exchanged Kunipia clay: It was prepared as in part (c) taking Kunipia clay instead of K10 montmorillonite.
d) $Al^{3+}$—exchanged catalyst: $Al^{3+}$—exchanged catalyst was prepared in the same manner as in part (c) stirring 1 lt. aqueous solution of $AlCl_3$ (1.0 M) and 80 g of K10 montmorillonite.
e) $Zn^{2+}$—exchanged catalyst: It was prepared in the same manner as in part (c) stirring 1M solution of $ZnCl_2$ and 80 g of K10 montmorillonite.

f) $Cu^{2+}$—exchanged catalyst: It was prepared in the same manner as in part (c) stirring 1M solution of $CuCl_2$ and 80 g of K10 montmorillonite.

g) $La^{3+}$—exchanged catalyst: It was prepared in the same manner as in part (c) stirring 1M solution of $LaCl_3$ and 80 g of K10 montmorillonite.

h) FePILC from K10 montmorillonite: The Na-montmorillonite was prepared by suspending and stirring commercial K10 in excess aqueous sodium chloride solution for 24 h. The Na-montmorillonite was separated by centrifugation and washed free of chloride ions by deionized distilled water and air dried. The cation exchange capacity of the air-dried clay is 0.8 equi. Trinuclear acetato hydroxy-iron (III) nitrate; $Fe_3(OCOCH_3)_7OH.2H_2ONO_3$ was used as the cation source for exchanging with the Na-montmorillonite. It was prepared by dissolving 80.8 g of $Fe(NO_3)_3.5H_2O$ in 50 ml of ethyl alcohol. This was reacted with 140 ml acetic anhydride with the evolution of heat. The solution was then cooled in an ice bath and the resulting precipitate was separated and used without further purification in the pillaring procedure. Cation-exchange:

A 0.04 mole/l aqueous solution of trinuclear acetato-hydroxy-iron (III) nitrate (19.48 g) in 700 ml water was added to a stirred 1% Na-montmorillonite aqueous suspension (8 g of Na-mont in 800 ml of water). The mixture was stirred for 3 hrs at 40° C., separated by centrifugation and washed with water several times to remove excess iron ions and dried in air.

i) FePILC from Kunipia clay: It was prepared as in part (h) taking Kunipia clay instead of K10 montmorillonite.

EXAMPLE 2

A mixture of benzene (25 ml), and $Fe^{3+}$ montmorillonite or $Zn^{2+}$ montmorillonite (0.5 g) were taken in a 50 ml two-necked round-bottomed flask equipped with Dean-Stark apparatus. Fuming nitric acid (5 ml) was added dropwise into the reaction mixture. The reaction mixture was heated to reflux where upon the required amount of liberated water was collected in the Dean-Stark apparatus which usually takes 1.5 hr. Later on, the catalyst was filtered and the reaction mixture was concentrated to obtain the pure mononitrobenzene.

EXAMPLE 3

A mixture of benzene (25 ml) and $Zn^{2+}$ montmorillonite catalyst (0.5 g), were stirred in a 50 ml two-necked round-bottomed flask. Fuming nitric acid (5 ml) was added dropwise into the reaction mixture at r.t. and stirred for 1.5 hr. Later on, the catalyst was filtered and the reaction mixture was concentrated to obtain the pure mononitrobenzene.

EXAMPLE 4

A mixture of benzene (6 ml) and $Zn^{2+}$ montmorillonite catalyst (2 g, excess catalyst), were stirred in a 50 ml two-necked round-bottomed flask. Fuming nitric acid (4 ml) was added dropwise into the reaction mixture at r.t. and stirred for 1.5 hrs. Later on, the catalyst was filtered and the reaction mixture was concentrated to obtain the pure mononitrobenzene.

EXAMPLE 5

A mixture of benzene (25 ml) and $Zn^{2+}$ montmorillonite (0.5 g) were taken in a 50 ml two-necked round-bottomed flask equipped with a Dean-Stark apparatus. Fuming nitric acid (17 ml) was added dropwise into the reaction mixture and the reaction mixture was heated to reflux where upon the required amount of liberated water is collected in the Dean-Stark apparatus which usually takes 2 hrs. Later on, the catalyst was filtered and the reaction mixture is concentrated to obtain nitrobenzene.

EXAMPLE 6

Benzene (25 ml) was taken in a 50 ml two-necked round-bottomed flask equipped with a Dean-Stark apparatus. Fuming nitric acid (17 ml) was added dropwise into the reaction mixture and the reaction mixture was heated to reflux where upon the required amount of liberated water is collected in the Dean-Stark apparatus which usually takes 2 hrs. Later on, the catalyst was filtered and the reaction mixture was concentrated to obtain nitrobenzene.

EXAMPLE 7

Benzene (25 ml) was stirred in a 50 ml two-necked round-bottomed flask. Fuming nitric acid (5 ml) was added dropwise into the reaction mixture at r.t. and stirred for 1.5 hr. Then, the reaction mixture was concentrated to obtain the pure mononitrobenzene.

EXAMPLE 8

Benzene (25 ml) was taken in a 50 ml two-necked round-bottomed flask equipped with Dean-Stark apparatus. Fuming nitric acid (5 ml) was added dropwise into the reaction mixture. The reaction mixture was heated to reflux where upon the required amount of liberated water is collected in the Dean-Stark apparatus which usually takes 1.5 hr. Then the reaction mixture was concentrated to obtain the pure mononitrobenzene.

EXAMPLE 9

A mixture of toluene (25 ml), and $Fe^{3+}$ montmorillonite or $Zn^{2+}$ montmorillonite (0.5 g) were taken in a 50 ml two-necked round-bottomed flask equipped with Dean-Stark apparatus. Fuming nitric acid (5 ml) was added dropwise into the reaction mixture. The reaction mixture was heated to reflux where upon the required amount of liberated water was collected in the Dean-Stark apparatus which usually takes 1.5 hr. Later on, the catalyst was filtered and the reaction mixture was concentrated to obtain the mixture of nitrotoluenes.

EXAMPLE 10

A mixture of o-xylene (25 ml), and $Fe^{3+}$ montmorillonite or $Zn^{2+}$ montmorillonite (0.5 g) were taken in a 50 ml two-necked round-bottomed flask equipped with Dean-Stark apparatus. Fuming nitric acid (5 ml) was added dropwise into the reaction mixture. The reaction mixture was heated to reflux where upon the required amount of liberated water was collected in the Dean-Stark apparatus which usually takes 1.5 hr. Later on, the catalyst was filtered and the reaction mixture was concentrated to obtain the mixture of nitro o-xylenes.

EXAMPLE 11

A mixture of m-xylene (25 ml), and $Fe^{3+}$ montmorillonite or $Zn^{2+}$ montmorillonite (0.5 g) were taken in a 50 ml two-necked round-bottomed flask equipped with Dean-Stark apparatus. Fuming nitric acid (5 ml) was added dropwise into the reaction mixture. The reaction mixture was heated to reflux where upon the required amount of liberated water was collected in the Dean-Stark apparatus which usually takes 1.5 hr. Later on, the catalyst was filtered and the reaction mixture was concentrated to obtain the mixture of nitro m-xylenes.

EXAMPLE 12

A mixture of p-xylene (25 ml), and $Fe^{3+}$ montmorillonite or $Zn^{2+}$ montmorillonite (0.5 g) were taken in a 50 ml two-necked round-bottomed flask equipped with Dean-Stark apparatus. Fuming nitric acid (5 ml) was added dropwise into the reaction mixture. The reaction mixture was heated to reflux where upon the required amount of liberated water was collected in the Dean-Stark apparatus which usually takes 1.5 hr. Later on, the catalyst was filtered and the reaction mixture was concentrated to obtain the nitro p-xylene.

EXAMPLE 13

A mixture of anisole (25 ml), and $Fe^{3+}$ montmorillonite or $Zn^{2+}$ montmorillonite (0.5 g) were taken in a 50 ml two-necked round-bottomed flask equipped with Dean-Stark apparatus. Fuming nitric acid (5 ml) was added dropwise into the reaction mixture. The reaction mixture was heated to reflux where upon the required amount of liberated water was collected in the Dean-Stark apparatus which usually takes 1.5 hr. Later on, the catalyst was filtered and the reaction mixture was concentrated to obtain the mixture of nitro anisoles.

EXAMPLE 14

A mixture of chlorobenzene (25 ml), and $Fe^{3+}$ montmorillonite or $Zn^{2+}$ montmorillonite (0.5 g) were taken in a 50 ml two-necked round-bottomed flask equipped with Dean-Stark apparatus. Fuming nitric acid (5 ml) was added dropwise into the reaction mixture. The reaction mixture was heated to reflux where upon the required amount of liberated water was collected in the Dean-Stark apparatus which usually takes 1.5 hr. Later on, the catalyst was filtered and the reaction mixture was concentrated to obtain the mixture of nitrochlorobenzenes.

EXAMPLE 15

A mixture of chlorobenzene (25 ml) and $Zn^{2+}$ montmorillonite catalyst (0.5 g), were stirred in a 50 ml two-necked round-bottomed flask. Fuming nitric acid (5 ml) was added dropwise into the reaction mixture at r.t. and stirred for 1.5 hr. Later on, the catalyst was filtered and the reaction mixture was concentrated to obtain the mixture of nitrochlorobenzenes.

EXAMPLE 16

A mixture of chlorobenzene (6 ml) and $Zn^{2+}$ montmorillonite catalyst (2 g, excess catalyst), were stirred in a 50 ml two-necked round bottomed flask. Fuming nitric acid (4 ml) was added dropwise into the reaction mixture at r.t. and stirred for 1.5 hrs. Later on, the catalyst was filtered and the reaction mixture was concentrated to obtain the mixture of nitrochlorobenzenes.

EXAMPLE 17

A mixture of chlorobenzene (25 ml) and $Zn^{2+}$ montmorillonite (0.5 g) were taken in a 50 ml two-necked round-bottomed flask equipped with a Dean-Stark apparatus. Fuming nitric acid (17 ml) was added dropwise into the reaction mixture and the reaction mixture was heated to reflux where upon the required amount of liberated water is collected in the Dean-Stark apparatus which usually take 2 hrs. Later on, the catalyst was filtered and the reaction mixture was concentrated to obtain the mixture of nitrochlorobenzenes.

EXAMPLE 18

Chlorobenzene (25 ml) was taken in a 50 ml two-necked round-bottomed flask equipped with a Dean-Stark apparatus. Fuming nitric acid (17 ml) was added dropwise into the reaction mixture and the reaction mixture was heated to reflux where upon the required amount of liberated water is collected in the Dean-Stark apparatus which usually take 2 hrs. Later on, the catalyst was filtered and the reaction mixture was concentrated to obtain the mixture of nitrochlorobenzenes.

EXAMPLE 19

Chlorobenzene (25 ml) was stirred in a 50 ml two-necked round-bottomed flask. Fuming nitric acid (5 ml) was added dropwise into the reaction mixture at r.t. and stirred for 1.5 hr. Then, the reaction mixture was concentrated to obtain the mixture of nitrochlorobenzenes.

EXAMPLE 20

Chlorobenzene (25 ml) was taken in a 50 ml two-necked round-bottomed flask equipped with Dean-Stark apparatus. Fuming nitric acid (5 ml) was added dropwise into the reaction mixture. The reaction mixture was heated to reflux where upon the required amount of liberated water is collected in the Dean-Stark apparatus which usually takes 1.5 hr. Then the reaction mixture was concentrated to obtain the mixture of nitrochlorobenzenes.

EXAMPLE 21

Naphthalene (13.62 g), $Zn^{2+}$ montmorillonite (0.25 g) and $CCl_4$ were stirred in 50 ml two-necked round-bottomed flask equipped with Dean-Stark apparatus. Fuming nitric acid (5 ml) was added dropwise into the reaction mixture. The reaction mixture was heated to reflux where upon the required amount of liberated water is collected in the Dean-Stark apparatus which usually takes 1 hr. Later on, the catalyst was filtered and the organic layer is concentrated to obtain 1-nitronaphthalene.

Yield:–74%

The results are given in Table 1, Table 2 and Table 3.

TABLE 1

Nitration of Chlorobenzene[a] with various catalysts:-

| Sl. No. | Catalyst | Temp. (° C.) | Conversion (%) | Isolated Yield (g) | Isomers[b] (o/p) |
|---|---|---|---|---|---|
| 1. | $Al^{3+}$ Mont. | 145 | 48.3 | 8.12 | 37.4:62.6 |
| 2. | $La^{3+}$ Mont. | 145 | 58.3 | 9.80 | 37.0:63.0 |
| 3. | $Cu^{2+}$ Mont. | 145 | 58.8 | 9.88 | 37.4:62.6 |
| 4. | $H^+$ Mont. | 145 | 51.6 | 8.68 | 37.1:62.9 |
| 5. | K10 Mont. | 145 | 64.2 | 10.80 | 37.3:62.7 |
| 6. | $Fe^{3+}$ Mont. | 145 | 77.3 | 13.00 | 36.0:64.0 |
| 7. | $Fe^{3+}$ Kunipia Mont. | 145 | 78.1 | 13.14 | 36.0:64.0 |
| 8. | Fe K10 PILC | 145 | 73.6 | 12.38 | 35.0:65.0 |
| 9. | Fe Kunipia PILC | 145 | 75.4 | 12.68 | 34.5:65.5 |
| 10. | $Zn^{2+}$ Mont. | 145 | 82.2 | 13.83 | 38.0:62.0 |

[a]The reactions were carried out as in example 14 by various metal catalysts
[b]by NMR; ratios of major isomers are given.

TABLE 2

Nitration of Benzene and Chlorobenzene with various amounts of Fum. $HNO_3$:-

| Sl. No. | Example[a] | Aromatic | Amount of Acid (ml) | Catalyst | Temp (° C.) | Conversion (%) | Isolated Yield (g) |
|---|---|---|---|---|---|---|---|
| 1. | 2 | Benzene | 5 | $Zn^{2+}$ Mont. | 115 | 92.8 | 12.00 |
| 2. | 8 | Benzene | 5 | Blank | 115 | 56.2 | 7.26 |
| 3. | 3 | Benzene | 5 | $Zn^{2+}$ Mont. | R.T. | 47.8 | 6.17 |
| 4. | 7 | Benzene | 5 | Blank | R.T. | 28.6 | 3.70 |
| 5. | 5 | Benzene[b] | 17 | $Zn^{2+}$ Mont. | 115 | 99.1[c] | 39.50 |
| 6. | 6 | Benzene[b] | 17 | Blank | 115 | 65.8[c] | 26.21 |
| 7. | 4 | Benzene | 4 | $Zn^{2+}$ Mont. excess | R.T. | 82.0[c] | 6.64 |
| 8. | 14 | Chlorobenzene | 5 | $Zn^{2+}$ Mont. | 145 | 82.2 | 13.83 |
| 9. | 20 | Chlorobenzene | 5 | Blank | 145 | 57.7 | 9.70 |
| 10. | 15 | Chlorobenzene | 5 | $Zn^{2+}$ Mont. | R.T. | 61.4 | 10.33 |
| 11. | 19 | Chlorobenzene | 5 | Blank | R.T. | 36.9 | 6.20 |
| 12. | 16 | Chlorobenzene | 17 | $Zn^{2+}$ Mont. | 145 | 99.9[c] | 38.70 |
| 13. | 17 | Chlorobenzene | 17 | Blank | 145 | 61.4[c] | 23.80 |
| 14. | 18 | Chlorobenzene | 4 | $Zn^{2+}$ Mont. excess | R.T. | 85.0[c] | 7.09 |

[a]as exemplified in the text
[b]5 ml of benzene was taken in Dean-Stark collector
[c]based on aromatics by G.C. analysis

TABLE 3

Nitration of Aromatics with Fum. $HNO_3$:-

| Sl. No. | Example[a] | Aromatic | Catalyst | Temp. (° C.) | Conversion (%) | Isolated yield (g) | Isomers (o/p)[b] |
|---|---|---|---|---|---|---|---|
| 1 | 2 | Benzene | $Fe^{3+}$-mont | 115 | 88.3 | 11.4 | — |
| 2 | 2 | Benzene | $Zn^{2+}$-mont | 115 | 92.8 | 12.0 | — |
| 3 | 9 | Toluene | $Fe^{3+}$-mont | 125 | 73.9 | 10.8 | 53.0:47.0 |
| 4 | 9 | Toluene | $Zn^{2+}$-mont | 125 | 77.2 | 11.5 | 51.7:48.3 |
| 5 | 14 | Chlorobenzene | $Fe^{3+}$-mont | 145 | 77.3 | 13.0 | 36.0:64.0 |
| 6 | 14 | Chlorobenzene | $Zn^{2+}$-mont | 145 | 82.2 | 13.8 | 38.0:62.0 |
| 7 | 10 | o-Xylene | $Fe^{3+}$-mont | 150 | 56.8 | 9.2 | 47.0[c]:53.0[d] |
| 8 | 10 | o-Xylene | $Zn^{2+}$-mont | 150 | 58.7 | 9.5 | 48.0[c]:52.0[d] |
| 9 | 12 | p-Xylene | $Fe^{3+}$-mont | 145 | 63.8 | 10.3 | — |
| 10 | 12 | p-Xylene | $Zn^{2+}$-mont | 145 | 68.1 | 11.0 | — |
| 11 | 11 | m-Xylene | $Fe^{3+}$-mont | 145 | 56.50 | 9.1 | 16.0[e]:84.0[f] |
| 12 | 11 | m-Xylene | $Zn^{2+}$-mont | 145 | 58.85 | 9.5 | 15.0[e]:85.0[f] |
| 13 | 13 | Anisole | $Fe^{3+}$-mont | 155 | 43.42 | 7.0 | 13.0:87.0 |
| 14 | 13 | Anisole | $Zn^{2+}$-mont | 155 | 46.00 | 7.5 | 12.0:88.0 |

[a]as exemplified in text.
[b]by NMR; ratios of major isomers are given.
[c]3-nitro-o-xylene;
[d]4-nitro-o-xylene;
[e]2-nitro-m-xylene;
[f]4-nitro-m-xylene The present process has several advantages as described below:
1. An ecofriendly process for production of aromatic nitro compounds with comparable activity when compared with the other conventional processes.
2. The support of the catalyst, clay is cheap and abundantly available in nature.
3. The use of sulphuric acid, a hazardous chemical is dispensed with.
4. The use of an expensive acetic anhydride which acts as water scavenger and nitrating agent in some of the processes considered to be an alternative is also dispensed with.
5. The present process envisages no disposable problem as the catalyst can be used for several recycles. The catalyst was subjected to 4 cycles which displayed almost consistent activity.
6. The present process is environmentally safe since there is no effluent disposable problem.

What is claimed is:

1. A process for preparing nitroaromatic compounds from aromatic hydrocarbons which comprises: nitrating aromatic hydrocarbons in the liquid phase using a nitrating agent which consists essentially of fuming nitric acid in the molar ratio of nitric acid to aromatic hydrocarbon of 0.3:1 to 1.2:1 in the presence of metal ion exchanged clay catalyst, wherein the metal ion is selected from the group consisting of $La^{3+}$, $Cu^{2+}$, $Fe^{3+}$ and $Zn^{2+}$, for 0.25 to 2.0 hrs and recovering the nitroaromatic compounds.

2. A process as claimed in claim 1, wherein aromatic hydrocarbons used are selected from benzene, chlorobenzene, toluene, o-xylene, m-xylene, p-xylene, anisole and naphthalene.

3. A process as claimed in claim 1, wherein recovery of nitroarenes is carried out by separating the catalyst by filtration and removing the excess aromatic hydrocarbons by distillation or by concentration in rotavapor.

4. A process as claimed in claim 2, wherein recovery of nitroarenes is carried out by separating the catalyst by filtration and removing the excess aromatic hydrocarbons by distillation or by concentration in rotavapor.

* * * * *